(12) United States Patent
Jones et al.

(10) Patent No.: US 7,592,049 B2
(45) Date of Patent: *Sep. 22, 2009

(54) DRY CHEMICALLY BOUND NONWOVENS WHICH ARE FLUSHABLE AND DISPERSIBLE

(75) Inventors: Ronald Bernal Jones, Allentown, PA (US); Blaine Richard Hobar, Ashfield, PA (US); Joel Erwin Goldstein, Allentown, PA (US); Lisa Ann Mercando, Pennsburg, PA (US)

(73) Assignee: Wacker Chemical Corporation, Adrian, MI (US)

( * ) Notice: Subject to any disclaimer, the term of this patent is extended or adjusted under 35 U.S.C. 154(b) by 169 days.

This patent is subject to a terminal disclaimer.

(21) Appl. No.: 11/181,051

(22) Filed: Jul. 14, 2005

(65) Prior Publication Data

US 2007/0015423 A1    Jan. 18, 2007

(51) Int. Cl.
*B05D 1/00* (2006.01)
*B05D 1/36* (2006.01)

(52) U.S. Cl. .................. 427/402; 427/203; 427/412

(58) Field of Classification Search ................. 427/203, 427/372.2, 384, 402, 412
See application file for complete search history.

(56) References Cited

U.S. PATENT DOCUMENTS

| 4,245,744 | A | | 1/1981 | Daniels et al. | |
|---|---|---|---|---|---|
| 4,333,464 | A | * | 6/1982 | Nakano | 604/364 |
| 5,252,332 | A | | 10/1993 | Goldstein | |
| 5,256,417 | A | | 10/1993 | Koltisko | |
| 5,384,189 | A | | 1/1995 | Kuroda et al. | |
| 5,629,081 | A | | 5/1997 | Richards et al. | |
| 5,972,805 | A | | 10/1999 | Pomplun et al. | |
| 5,976,694 | A | | 11/1999 | Tsai et al. | |
| 6,121,170 | A | | 9/2000 | Tsai et al. | |
| 6,429,261 | B1 | * | 8/2002 | Lang et al. | 525/191 |
| 6,495,080 | B1 | | 12/2002 | Tsai et al. | |
| 6,599,848 | B1 | | 7/2003 | Chen et al. | |
| 6,815,502 | B1 | | 11/2004 | Lang et al. | |
| 2005/0239359 | A1 | * | 10/2005 | Jones et al. | 442/154 |

FOREIGN PATENT DOCUMENTS

JP    49-31970 A  *  3/1974
WO   WO 00/39378      7/2000

* cited by examiner

*Primary Examiner*—William Phillip Fletcher, III
(74) *Attorney, Agent, or Firm*—RatnerPrestia

(57) ABSTRACT

This invention is directed to methods of incorporating a trigger such as boric acid, boric acid salts, sodium sulfate, or other salts, into a nonwoven web substrate for the preparation of dry nonwoven products which are redispersible when put in contact with large amounts of water or liquid. In one method, the trigger is in a dry powder form and is incorporated into the nonwoven fibers followed by treatment of the fibers with an aqueous redispersible binder, and binding and drying the web. Another method is to saturate a dry bonded nonwoven web with an aqueous solution of the trigger and then dry the saturated web. Yet another method is to apply an aqueous solution of the trigger to the web followed by applying a redispersible aqueous binder to the web and then heating and drying the web.

8 Claims, No Drawings

DRY CHEMICALLY BOUND NONWOVENS WHICH ARE FLUSHABLE AND DISPERSIBLE

BACKGROUND OF THE INVENTION

The issue of disposability of products is of great concern to the nonwovens industry. Among the different types of disposable nonwovens are pre-moistened nonwovens which are readily dispersible in large amounts of water or liquids, and absorbent, disposable nonwovens that can be used as wipes and require a high level of strength after contact with liquids.

In recent years a large number of wipes and wiper products have been introduced which claim that they can be flushed after use. Most of these products are flushable based on size; i.e., the wipe or wiper is small enough to pass through the opening at the bottom of the toilet and pass through the plumbing and sewer lines under ideal conditions. These products are generally based on hydroentangled nonwoven webs which do not break up in the flushing process. These products can compromise sewer or drain lines in several ways. If a larger than recommended number of wipes are flushed (for example, by a child) these wipes can get stuck in pipe elbows, create a plug which prevents water from passing and creating a back up. Also these wipes can get caught on tree roots which sometimes protrude into sewer lines creating plugs and back ups. It is highly desirable for these nonwoven wipes or wipers to disperse allowing the webs to break up into individual cellulose fibers which can more easily pass the obstacles encountered in the sewer and drain lines.

With regard to dispersible nonwovens, the products may be produced as dry material, such as tissues or wipes, which will be truly flushable and dispersible when deposited in a large amount of water or aqueous solution. The tissues or wipes must disintegrate in water under gentle agitation without the addition of temperature or chemicals.

Water soluble or redispersible polymeric binders have been used in making nonwoven substrates and they are generally comprised of poly(vinyl alcohol) (PVOH), PVOH-stabilized vinyl acetate or vinyl acetate based polymers, e.g., vinyl acetate-ethylene (VAE) emulsion polymers. The treated dry nonwoven webs needs to have enough wet strength so that they will not disintegrate during use but will disintegrate in the presence of excess water such as the water in a toilet. Many current commercial nonwoven webs have either no wet strength or have a lot of permanent wet strength. The former are unsuitable for use in products such as feminine hygiene products because they fall apart on insult. The latter cannot be safely discarded in toilets without the risk of clogging pipes.

Several methods have been proposed to address disintegration of a dry nonwoven product during use. One method employs the addition of boric acid or derivatives to the aqueous lotion composition which is applied to a nonwoven substrate in order to maintain the integrity of the nonwoven substrate. The following patents illustrate the prior art of this technology:

U.S. Pat. No. 4,245,744 discloses nonwoven fiber sheets impregnated with PVOH-containing vinyl acetate-based polymers in which the nonwoven sheets are maintained in contact with a dilute aqueous solution of a precipitating or gelling agent for PVOH, such as boric acid.

U.S. Pat. No. 5,252,332 discloses a packaged towelette comprising a sheet of nonwoven fibers impregnated with PVOH or a PVOH-containing binder in contact with an aqueous solution containing boric ions and bicarbonate ions.

U.S. Pat. No. 5,629,081 discloses a pre-moistened, dispersible and biodegradable wet wipe comprising a web of nonwoven fibers contacted with a PVOH-containing binder. The binder-contacted web further comprises an aqueous lotion solution comprising 0.1-0.9 wt % boric acid and 5-8 wt % alkali metal bicarbonate, based on weight of the lotion.

U.S. Pat. No. 5,384,189 discloses a water decomposable nonwoven fabric in which the fibers are bonded to one another with a water-soluble binder comprising an unsaturated carboxylic acid/unsaturated carboxylic acid ester copolymer in which 1-60 mole % of the repeating units derived from the carboxylic acid is in the form of a salt. The binder is soluble in tap water but is insoluble in an aqueous solution containing not less than 0.5 wt % of a neutral inorganic salt comprising a monovalent ion.

U.S. Pat. No. 5,972,805 discloses a water-soluble polymeric binder composition for use in making nonwoven webs comprising 25-90 wt % unsaturated carboxylic acid/unsaturated carboxylic acid esters/ester copolymer, 10-75 wt % divalent ion inhibitor and 0-10 wt % plasticizer. The water-soluble binder composition is soluble in an aqueous environment having a divalent ion concentration of less than about 50 ppm and a monovalent concentration of less than about 0.5 wt %.

U.S. Pat. No. 5,256,417 discloses a packaged towelette which is disposable and comprises a sheet of nonwoven fibers impregnated with a binder, e.g., PVOH or an aqueous polymer emulsion containing PVOH as a protective colloid. The sheet is maintained in a wet condition within the package by contact with a non-aqueous lotion composition which is a liquid organic compound that is a non-solvent for PVOH.

U.S. Pat. Nos. 5,976,694 , 6,121,170, and 6,495,080 disclose disposable products which are flushable. A feature of the flushable product is that it has sufficient wet strength for its intended use but loses its structural integrity upon contact with large amounts of water. The compositions employed in forming the disposable product comprise a blend of at least one water-sensitive polymer and at least one polymer selected from polylactide, polyolefin-grafted with a polar group, e.g., maleic acid, and other aliphatic polyesters. Dispersibility depends upon the amount of monovalent or multivalent ions in the aqueous solution.

WO 00/39378 discloses a water-dispersible nonwoven fabric containing a temperature-sensitive or ion-sensitive binder material, which is useful in the manufacture of flushable personal care products.

Additives such as boric acid and mono- or multi-valent ions are typically called triggers in the industry. These triggers interact with water soluble binders to increase wet tensile strength of the web. This allows the webs, bound with a combination of water soluble binder and trigger, to function in applications such as wet wipes, where the web needs to maintain its integrity under conditions of use. When the web is placed in excess water (i.e., in a toilet bowl) the concentration of these triggers is diluted, breaking up the interaction between the binder and trigger and causing a loss of wet tensile strength. When the wet tensile strength of the web is diminished, it can break up under agitation and separate into smaller pieces which can more easily pass through the drain and sewer lines.

For pre-moistened products, airlaid webs can be manufactured with water soluble binders and the trigger can be added to the lotion creating the interaction.

There is a need in the industry for improved and economical methods of incorporating triggers into dry nonwoven products. The method should result in a product which maintains its integrity when made wet or damp, but enable complete dispersion in large amounts of water or aqueous liquids such as is found in toilets.

BRIEF SUMMARY OF THE INVENTION

This invention is directed to methods of incorporating a trigger such as boric acid, boric acid salts, sodium sulfate, or other organic or inorganic salts into a dry nonwoven web. In one method, the trigger is in a dry powder form and is added to the nonwoven fibers before the fibers are treated with an aqueous redispersible binder. This can be accomplished by mixing the dry powdered trigger with the fibers in a single line or in alternative lines with the aqueous binder. This technique is commonly used in dosing superabsorbent powder (SAP) to nonwoven fabrics. After treatment with the aqueous redispersible binder, the treated nonwoven web of fibers are heated to bind the fibers and dry the web.

Another method for adding the trigger is to spray a dry bonded nonwoven web with an aqueous solution of the trigger or soak a dry bonded nonwoven web in an aqueous solution of the trigger and then dry the saturated web.

Yet another method for adding the trigger is to apply an aqueous solution of the trigger to the web followed by applying a redispersible aqueous binder to the web and then heating and drying the web.

Use of one of the above methods of incorporating a trigger into a nonwoven web substrate results in a dry nonwoven product with good integrity when made wet or damp during use; but which will disintegrate when subjected to large amounts of water or liquids such as are found in toilets.

With flushable pre-moistened wipes, the trigger is carried in the lotion that are used to moisten the wipes. In this invention, a lotion does not need to be applied to the nonwoven web in order to incorporate the trigger into the dry nonwoven web.

DETAILED DESCRIPTION OF THE INVENTION

The trigger can be incorporated into the nonwoven web fibers before or after the web is bound with an aqueous redispersible binder. Examples of triggers are boric acid, sodium tetraborate and other boric acid salts, sodium sulfate, sodium citrate, and other organic or inorganic salts. Salts serve as water-binding compounds and may be added to the aqueous composition to assist in preventing the dissolution of the water-soluble polymeric binder. The amount of the water-binding materials and/or trigger can range from 3 to about 100 wt %, preferably 5-95 wt %, and most preferably 20-90 wt %, of the aqueous solids, i.e., the components other than water comprising the aqueous composition. Water binding compounds include ammonium, mono- and polyvalent metal salts of inorganic and organic acids. Suitable metals include alkali metals, such as lithium, sodium, and potassium, and alkaline earth metals, such as magnesium and calcium. Suitable acid moieties include organic acids such as carbonic acid, citric acid, acetic acid and succinic acid and inorganic acids such as phosphoric acid, sulfuric acid and hydrochloric acid. Exemplary salts include sodium chloride, sodium sulfate, sodium acetate, sodium citrate, sodium carbonate, sodium bicarbonate, sodium lauryl sulfate, disodium laureth sulfosuccinate, sodium laureth sulfate, sodium nonylphenol ethoxylate sulfate, disodium phosphate, sodium carbonate, and their ammonium or potassium counterparts.

If the trigger is applied to the web after the web is bound with a binder, the bound web is soaked or sprayed with an aqueous solution of the trigger. The web is then dried, leaving the trigger embedded in the web.

If the trigger is applied before the web is bound with the binder, the trigger can be incorporated by adding it, in dry form, to the pulp when it leaves the hammermill or at some point after it is transferred from the hammermill. For example, it can be added to the pulp in one, some, or all of the headboxes by dropping it onto the pulp from above the moving felt. It can also be added by free fall between two or more headboxes or by any method currently used or known to add superabsorbent powders to nonwoven webs. If added as a dry trigger, it should be in powder or particulate form. In general, the particle size should be small enough to enable the particles to fall into the spaces between the fibers and to maximize surface area and interaction with the binder. Particle size, i.e., average particle diameter, can be from about 50 to 2000 microns; typically about 200 to 750 microns.

The amount of dry trigger added to the nonwoven web can be 1 to 50% of the weight of the finished web. The amount will depend on the type of trigger used and the application for the finished web. Typical amounts of trigger are 5 to 40% by weight and 10 to 30% by weight of the finished web. However the range can be any combination of 1 to 50% by weight Another way to add the trigger before the binder is applied is to spray or saturate the unbound web with an aqueous solution of the trigger and then apply the aqueous binder. This procedure can be done more than one time to increase the level of trigger and/or binder, depending on the performance objectives of the treated web.

The water redispersible latex polymeric binder for dispersible nonwoven products is one that is generally non-crosslinking, i.e., it does not contain polymerized NMA units which cross link to the extent the polymer becomes relatively nonredispersible. Addition of external crosslinkers are also not desirable. These lattices can either be surfactant protected or stabilized with a protective colloid like PVOH or HEC. Most desirably the water redispersible latex polymer contains PVOH as the protective colloid as a component of the stabilizing system in its preparation by aqueous emulsion polymerization. PVOH stabilized vinyl acetate and vinyl acetate based polymers, e.g., VAE polymer emulsions are preferred due to their ease of water dispersibility. Acrylic polymers, acrylic copolymers, and styrene butadiene copolymers which are either PVOH or surfactant protected are also appropriate for this application.

The water redispersible binder for the nonwoven webs can also be a blend of a latex as described above with PVOH. These latex/PVOH blends can also contain additives such as poly(acrylic acid), starch, and various humectants or additives with hydroxyl or carboxyl functionality. The PVOH portion of the formulation can be any hydrolysis from 70 to 100%. Copolymers of PVOH, such as sulfonated materials or poly(vinyl alcohol/vinyl amine), or blends of PVOH of different molecular weights and/or hydrolysis can also be used in the latex blends. Furthermore, the binder can be a member of a family of ion-sensitive water dispersible polymers disclosed in U.S. Pat. Nos. 6,815,502 and 6,599,848, and references cited therein. Examples of commercial binders are VINAC® 911 and VINAC 912 vinyl acetate-poly(vinyl alcohol) polymer emulsions.

Water redispersible latex polymeric binders that can be used include but are not limited to vinyl acetate based polymers, e.g., either vinyl acetate homopolymers or VAE polymers stabilized with PVOH and having a Tg of −45° C. to 50° C. There can also be low levels of other monomers polymerized into the VAE polymer backbone. These monomers can include (meth)acrylic acid, crotonic acid, alkyl(meth)acrylates where the alkyl group is $C_1$-$C_{12}$, linear or branched, di- or mono-alkyl maleates where the alkyl group is $C_1$-$C_{12}$, linear or branched, (meth)acrylamide, di- or mono-alkyl substituted (meth)acrylamides where the alkyl group is $C_1$-$C_{12}$, linear or branched, vinyl esters of alkanoic acids where the alkyl group is $C_1$-$C_{12}$, linear or branched, propylene, vinyl chloride, and vinyl ethylene carbonate.

The PVOH employed as a component of the blend can have a degree of hydrolysis from 75 to 96 mole %; preferably, 87 to 89 mole %. It can also have a degree of hydrolysis of greater than 96 mole %. It is preferred to use PVOH having a high molecular weight; degree of polymerization (DPn) of 600 to 2500 or more. Increasing the degree of hydrolysis of the PVOH tends to result in a web which redisperses much slower. This property does not preclude the dispersions from being appropriate binders but they are less desirable in some applications. PVOH products are available commercially from Celanese Chemical Company and bear the registered tradename Celvol.

The term poly(acrylic acid) is intended to refer to polymer having a major portion (e.g., at least 50%) and preferably at least 90% of polymerized acrylic acid units in the polymer backbone. Often poly(acrylic acid) is formed by the hydrolysis of poly(acrylamide) and thus residual acrylamide can be present in the polymer. The polymer can also have any molecular weight, but a preferred number average molecular weight range for the poly(acrylic acid) is 100,000 to 500,000 Daltons. Examples of commercially appropriate poly(acrylic acid) include Acumer® 1540 and Acumer 1510 which are available from Rohm & Haas, Cyanamer® A-15, Cyanamer A-100L, Cyanamer P-21, Cyanamer A-370 available from Cytec Industries, Inc., Alcosperse 124, Alcosperse 404, Alcosperse 406, Alcosperse 459, Alcosperse 602A and Alcosperse 747 available from Alco Chemical, and several grades of poly(acrylic acid) available from Aldrich Chemical Company.

The blend is applied to the fibrous web in an amount which is at least sufficient to bind the fibers together to form a self-sustaining web. The blend, calculated on a dry basis, is applied to the fibrous starting web in an amount generally from about 5-50 wt % preferably 15 to 30 wt % in the formation of the nonwoven web. After application of the blend, in aqueous form, the impregnated web is heated to temperatures sufficient to bind and dry the web. Temperatures for drying and binding can range from 190 to 350° F. (88 to 177° C.); typically 200 to 275° F. (93 to 135° C.). The trigger can then be applied to the bonded web by soaking the web in an aqueous solution of the trigger or by spraying the web with an aqueous solution of the trigger. The web is then dried to form a dry redispersible nonwoven web.

The binders are applied to the web either by spray, foam, saturation padding or another method known in the art. The amount of the binder present on the finished web can be between 5% to 30% of the weight of the finished web.

The dispersible nonwoven web is comprised of a nonwoven fibrous material. The fibrous material is primarily comprised of cellulose wood pulp fibers, typically with an added amount of textile fibers to enhance wet and dry strength. Typically, the wood pulp fibers comprise about 75-100 wt % and the textile fibers about 0-25 wt % of the nonwoven substrate. The preferred textile fibers include rayon, cotton, wool, acetate, or tencel fibers.

Wood pulp (alone or blended with natural or synthetic fibers) can be processed by dry (air-laid, carded, rando) or wet-laid processes to produce nonwovens webs. Nonwoven webs produced by air-laid processes are preferred due to minimal hydrogen bonding of fibers in the finished product compared to wet-laid nonwovens. Air-laid processes impart little or no inherent integrity to the web which must be overcome with agitation to achieve complete disintegration of the web.

In one method of forming a dispersible nonwoven web, the web is first coated or impregnated with a water soluble or water redispersible binder. This may be done by (1) immersing the webs, or running lengths of the web in an aqueous composition of the water redispersible latex polymeric binder, especially an aqueous polymer emulsion stabilized with PVOH as the protective colloid or (2) applying the water soluble or redispersible polymeric binder to the surfaces of the nonwoven web of fibers by spraying, by padding, by roller, or by other types of application known in the art.

Another method of forming the dry dispersible nonwoven web is to apply the trigger in dry powder form to nonwoven web fibers as the web of fibers or pulp leaves the hammermill or at some point after the web of fibers or pulp is transferred from the hammermill. The trigger, in powder form, can be added during the web forming process, similar to the process for adding superabsorbent powder (SAP) to airlaid webs. For example, the dry trigger can be added through SAP dosing lines to the fiber mix in the headbox during web formation. It can also be added into a hopper and "sprinkled" onto the web through oscillating screens either after or between the headboxes. This latter process is commonly used to apply powder binders to nonwoven webs. The trigger can also be dropped onto the web of fibers as it is transferred by a movable belt by any other method known in the art. Application of the trigger in dry powder form enables the particles of the trigger to be evenly dispersed into the web and maximizes the interaction between the trigger and binder. An aqueous dispersible binder is then applied to the web of fibers containing the trigger by methods described above. The web fibers are then bonded and dried.

A third method for forming a dry dispersible nonwoven web is to apply an aqueous solution of a trigger to a web of nonwoven fibers as described above and then apply an aqueous dispersion of a redispersible binder to the web of nonwoven fibers as described above. Heat is then applied in order to bond the fibers and dry the web.

The following examples are intended to illustrate various embodiments of the invention and are not intended to restrict the scope thereof.

EXAMPLES

Table 1 below shows the performances of nonwoven webs that have been bound with dispersible binders and then saturated with two salt solutions. The procedure used to bind the web and then saturate the web with the salt or boric acid solutions was as follows: Webs bound with water soluble binder were treated with 300% of the web weight with aqueous solutions of the trigger. Concentrations for the salt solutions varied from 5-15% depending on desired add-on. Boric acid concentration was 4.4%. The binders used were VINAC 911 poly(vinyl acetate) and a VAE polymer emulsion containing approximately 80% by weight vinyl acetate and approximately 20% by weight ethylene and having a $T_g$ of about 0° C. The binders also contained poly(vinyl alcohol) as stabilizer.

The tensile data are in grams per inch (g/in) of load. The test method is TAPPI T494.

Lotionized tensile strength was accomplished using the Intron test procedure above. Samples were lotionized with the lotion containing 10% sodium sulfate or 4.4% boric acid, prior to testing and after binding at 300% of the web weight.

Flushability was assessed by flushing the test specimens in an American Standard toilet with 1.6 gallons of water/flush. Samples to be evaluated were placed in the toilet for 15 seconds to allow the sample to be uniformly wetted by the toilet water. The sample was then flushed down the toilet, through a 90° angle tube at the toilet exit and collected on a mesh screen. Dispersibility was subjectively assessed using web integrity as the factor to determine if the sample was dispersed. If the sample was still in tact it was flushed again and reassessed. If the sample was still in tact after 5 flushes, the testing was stopped and the sample was determined to be non-flushable.

soluble binder plus trigger systems were comparable to the lotionized tensile strength of the binders in samples 1-4. These products dispersed in 3-5 flushes.

Table 2 below shows the performance properties of webs that were prepared as follows: Binders were applied to a 55 gsm web at 10% add-on and dried. Binders evaluated were VINAC 911 poly(vinyl acetate), a VAE polymer emulsion as in Table 1, and a 70/30 dry blend of AIRFLEX 400 vinyl

TABLE 1

| Sample | Binder Composition | Web Wt, gsm | % Binder Add-on | Dry Tensile | Wet Tensile | Lotionized Tensile (10% $Na_2SO_4$) | Nbr of Flushes | Lotionized Tensile (4.4% $H_3BO_3$) | Nbr of Flushes |
|---|---|---|---|---|---|---|---|---|---|
| 1 | VINAC 911 PVAc | 135 | 9.1 | 3417.9 | 99.7 | 303.6 | <2 | 658 | <3 |
| 2 | VINAC 911 PVAc | 90 | 10.6 | 2986.1 | 89.7 | 259.5 | 2 | 508.0 | 2 |
| 3 | VAE polymer Emulsion | 135 | 9.0 | 4281.8 | 173.1 | 765.7 | <3 | 1309.9 | <4 |
| 4 | VAE | 90 | 10.6 | 3144.3 | 93.9 | 455.6 | <3 | 971.0 | 4 |
| 5 | VINAC 911 PVAc + 10% $Na_2SO_4$* | 135 | 8.3 | 3687.0 | 220.0 | N/A | | N/A | 4** |
| 6 | VINAC 911 PVAc + 10% $Na_2SO_4$* | 90 | 9.7 | 3495.5 | 174.0 | N/A | | N/A | <3** |
| 7 | VAE + 10% $Na_2SO_4$* | 135 | 8.0 | 5162.5 | 513.1 | N/A | | N/A | <5** |
| 8 | VAE + 10% $Na_2SO_4$* | 90 | 10.5 | 3689.2 | 364.9 | N/A | | N/A | <5** |
| 9 | VINAC 911 PVAc + 4.4% $H_3BO_3$* | 135 | 8.1 | 3754.5 | 418.4 | N/A | | N/A | <5** |
| 10 | VINAC 911 PVAc + 4.4% $H_3BO_3$* | 90 | 10.6 | 2769.0 | 421.6 | N/A | | N/A | 3** |
| 11 | VAE + 4.4% $H_3BO_3$* | 135 | 8.8 | 4720.8 | 1109.0 | N/A | | N/A | <5** |
| 12 | VAE + 4.4% $H_3BO_3$* | 90 | 10.9 | 3523.7 | 909.7 | N/A | | N/A | >5** |

*$Na_2SO_4$ and $H_3BO_3$ concentration based on total web weight
**Unlotionized Samples 1-4 in the table above represent airlaid webs bound with VAE or poly(vinyl acetate) polymer emulsion binders. Web basis weights were 90 and 135 grams per square meter (gsm) for both binders. As can be seen from the data, each binder provided a high degree of dry tensile strength to the nonwoven web. However when wet tensile strength was measured, more than 95% of the tensile strength was lost. If these webs were lotionized to make wet wipes for example, wet strength was improved 5-10 fold by addition of either boric acid or sodium sulfate to the lotion. When these lotionized wipes were flushed, they completely dispersed in 2-4 flushes. Samples 5-12 show the performance of dry webs made by applying a combination of a water soluble binder and a trigger to a web of fibers and then drying and binding the web. Web weights were 90 and 135 gsm. Triggers were sodium sulfate and boric acid. The data show that these binders gave comparable dry tensile strength to the binders without trigger. However these was a 3-10 fold increase in wet tensile strength with the trigger in the web (samples 5-12) vs without (samples 1-4). The wet tensile strength of the water acetate polymer emulsion adhesive with CELVOL® 523 poly(vinyl alcohol). Acumer 1540 poly(acrylic acid) was added to the VINAC 911 poly(vinyl acetate) to determine the effect of poly(acrylic acid) on tensile strength. Each web was evaluated for dry tensile strength and wet tensile strength without a trigger. Then the trigger was added as a lotion at levels of 300%, 400% and 600% of the web weight of each sample and dried to incorporate a dry trigger into each web. Trigger solutions applied were 7.5% $Na_2SO_4$ and 4.4% boric acid. Flushability and wet tensile strength of the webs bound with the water soluble binder and trigger combinations were evaluated. The data show that adding the trigger to each binder resulted in a 2 to 5 fold increase in wet tensile strength of the web. All webs were determined to be flushable and dispersible as shown by complete dispersion in less than 5 flushes. Poly(acrylic acid) increased the wet tensile strength of both VINAC 911 and the AIRFLEX 400-CELVOL 523 system. However, based on the results, it was not necessary to utilize the poly(acrylic acid) to reach the desired performance level.

TABLE 2

| Property | VINAC-911 | VINAC-911 + 2% Acumer 1540 | VAE Emulsion Polymer | 70% Airflex 400 + 30% Celvol 523 |
|---|---|---|---|---|
| Dry Tensile, g/in | 912.9 | 1002.6 | 779.2 | 783.7 |
| Wet Tensile, g/in | 16.9 | 39.0 | 20.7 | 14.4 |
| Wet tensile, 300% loading of 7.5% NaSO$_4$ | 63.3 | 101.4 | 97.4 | 64.7 |
| Number of Flushes | 1 | <5 | 3 | 2 |
| Wet tensile, 400% loading of 7.5% Na$_2$SO$_4$ | 62.8 | 113.1 | 94.9 | 62.1 |
| Number of Flushes | 2 | 4 | 3 | <3 |
| Wet Tensile, 600% loading of 7.5% Na$_2$SO$_4$ | 58.9 | 107.8 | 79.7 | 57.8 |
| Number of Flushes | 2 | 5 | 3 | <3 |
| Wet tensile, 300% loading of 4.4% H$_3$BO$_3$ | 175.2 | 227.1 | 227.6 | 202.3 |
| Number of Flushes | <2 | 4 | 2 | 2 |
| Wet tensile, 400% loading of 4.4% H$_3$BO$_3$ | 193.2 | 237.9 | 220.7 | 202.3 |
| Number of Flushes | 2 | 3 | 3 | 2 |
| Wet tensile, 600% loading of 4.4% H$_3$BO$_3$ | 208.8 | 250.9 | 216.4 | 202.2 |
| Number of Flushes | 2 | 4 | 3 | 2 |

What is claimed is:

1. A method of making a dry bonded redispersible nonwoven web comprising:
   (a) applying dry particles selected from the group consisting of boric acid, an organic salt, and an inorganic salt, to a nonwoven web of fibers to form a nonwoven web of fibers containing the dry particles dispersed therein;
   (b) applying an aqueous dispersion of a redispersible binder to the nonwoven web of fibers containing the dry particles dispersed therein to form a wet nonwoven web of fibers; and
   (c) drying and binding the wet nonwoven web of fibers to form a fry redispersible nonwoven web.

2. The method of claim 1 wherein the organic salt or inorganic salt is an ammonium, an alkali metal or an alkaline earth metal salt of carbonic acid, citric acid, acetic acid, succinic acid, phosphoric acid, sulfuric acid or hydrochloric acid.

3. The method of claim 1 wherein the redispersible binder comprises a poly(vinyl alcohol) stabilized poly(vinyl acetate) polymer emulsion or a poly(vinyl alcohol) stabilized vinyl acetate-ethylene polymer emulsion formed by emulsion polymerization.

4. The method of claim 1 wherein the dry particles are applied to the web of nonwoven of fibers via superabsorbent particle dosing lines or are sprinkled onto the web through oscillating screens.

5. The method of claim 1 wherein the average diameter of the dry particles is about 50 to 2000 microns.

6. A method of making a dry bonded redispersible nonwoven web comprising:
   (a) applying an aqueous solution of an organic or inorganic salt selected from the group consisting of an ammonium, an alkali metal and an alkaline earth metal salt of carbonic acid, citric acid, acetic acid, succinic acid, phosphoric acid, sulfuric acid or hydrochloric acid, to a nonwoven web of fibers to form a wet nonwoven web of fibers;
   (b) applying an aqueous dispersion of a redispersible binder to the wet nonwoven web of fibers to form a wet nonwoven web of fibers containing a redispersible binder; and
   (c) drying and binding the wet nonwoven web of fibers containing a redispersible binder to form a dry bonded redispersible nonwoven web.

7. A method of making a dry bonded redispersible nonwoven web comprising:
   (a) applying an aqueous solution of an ammonium, an alkali metal or an alkaline earth metal salt of carbonic acid, citric acid, acetic acid, succinic acid, phosphoric acid, sulfuric acid or hydrochloric acid to a bonded nonwoven web of fibers to form a wet bonded nonwoven web of fibers;
   (b) drying the wet bonded nonwoven web of fibers to form a dry bonded redispersible nonwoven web.

8. The method of claim 7 wherein the redispersible binder comprises a poly(vinyl alcohol) stabilized poly(vinyl acetate) polymer emulsion or a poly(vinyl alcohol) stabilized vinyl acetate-ethylene polymer emulsion formed by emulsion polymerization.

* * * * *